United States Patent [19]
Viesturs

[11] Patent Number: 4,969,881
[45] Date of Patent: Nov. 13, 1990

[54] DISPOSABLE HYPERBARIC OXYGEN DRESSING

[75] Inventor: Eric Viesturs, Southbury, Conn.

[73] Assignee: Connecticut Artcraft Corp., Naugatuck, Conn.

[21] Appl. No.: 432,151

[22] Filed: Nov. 6, 1989

[51] Int. Cl.$^5$ .............................................. A61F 13/00
[52] U.S. Cl. ..................................... 604/305; 604/307; 128/156; 128/888; 424/443
[58] Field of Search ............... 128/155, 156, 847, 887, 128/888; 604/304, 307, 305; 424/443, 447, 445, 448, 449

[56] References Cited

U.S. PATENT DOCUMENTS 3,026,874  3/1962  Stevens ................................ 604/305
3,610,238 10/1971  Rich, Jr. ............................... 128/847
3,782,377  1/1974  Rychlik ................................. 128/888

FOREIGN PATENT DOCUMENTS 8301388  4/1983  World Int. Prop. O. .......... 604/305

Primary Examiner—David J. Isabella
Assistant Examiner—Paul Prebilic

[57] ABSTRACT

Disposable hyperbaric oxygen dressing adapted to treatment of a body sore on the skin of a patient. A thin flexible oxygen impermeable plastic film has upper and lower surfaces. A rigid flat open cell plastic member is oxygen permeable. The member has a central opening, a flat upper surface and a flat lower surface. The upper member surface is sealed to the lower surface of the film, the film-member seal being oxygen impermeable. A first self-adhesive layer is secured to the lower surface of the member. A second layer of release paper is removably secured to the first layer. The first layer, after the second layer has been removed, is adapted to be removably sealed in an oxygen impermeable manner to the skin of the patient with the sore being disposed in the opening. An oxygen feed tube extending through the member into the central opening, said tube being oxygen impermeable and sealed to the member, the tube-member seal being oxygen impermeable.

4 Claims, 1 Drawing Sheet

DISPOSABLE HYPERBARIC OXYGEN DRESSING

BACKGROUND OF THE INVENTION

It is well known that body sores on the skin of bedridden patients can be successfully treated by exposing such sores to a flow of oxygen in a small hyperbaric chamber detachably secured to the body and overlying the sores. Such chambers are expensive, must be sterilized after each use, and are difficult to secure properly in position.

The present invention is directed towards a disposable hyperbaric oxygen dressing which accomplishes the same function as the known chambers but which is much less expensive, is easily secured in position to the patient, is easily removed from the patient after use, and, since it is disposable, does not have to be sterilized after use.

SUMMARY OF THE INVENTION

A disposable hyperbaric oxygen dressing in accordance with the principles of the invention is adapted to treatment of a body sore on the skin of a patient. The dressing utilizes a thin flexible oxygen impermeable plastic sheet having upper and lower surfaces. The dressing also utilizes a rigid flat open cell plastic member which is oxygen permeable. The member has a central opening, a flat upper surface and a flat lower surface.

The upper member surface is sealed to the lower surface of the sheet, the sheet-member seal being oxygen impermeable. The lower member surface is adapted to be removably sealed to the skin of the patient with the sore being disposed in the opening. The skin-member seal is also oxygen impermeable.

An oxygen feed tube extends through the member into the central opening. Oxygen is supplied at an above atmospheric pressure through the tube into the opening and passes out of the opening through the open cell structure of the member, thus providing the requisite oxygen treatment. The feed tube is oxygen impermeable. The pressure of the incoming oxygen can be regulated, using a manually operable pressure reducing valve connected in the oxygen feed line between the oxygen source and the tube inlet, to maintain the oxygen pressure in the opening at a slight positive pressure with respect to the ambient air pressure. This is done by adjusting the pressure until the sheet exhibits a slight upward bulge in the region above the opening.

DETAILED DESCRIPTION OF PREFERRED EMBODIMENTS

Figure 1:
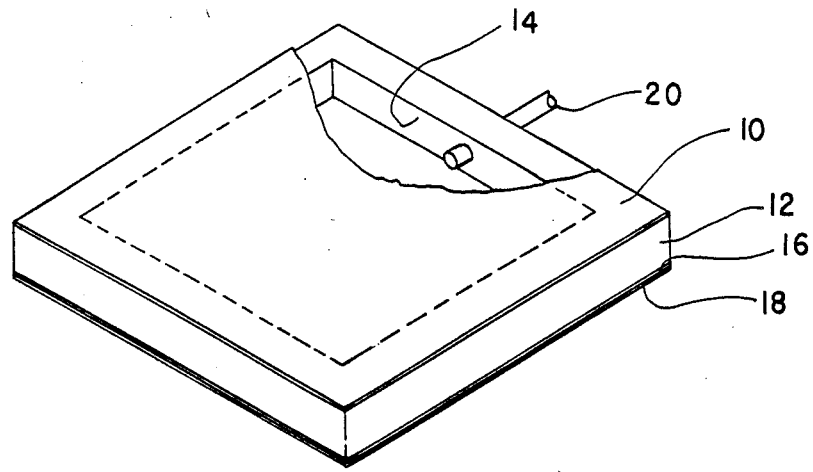
FIG. 1 is a perspective view of a preferred embodiment of the invention.
Figure 2:
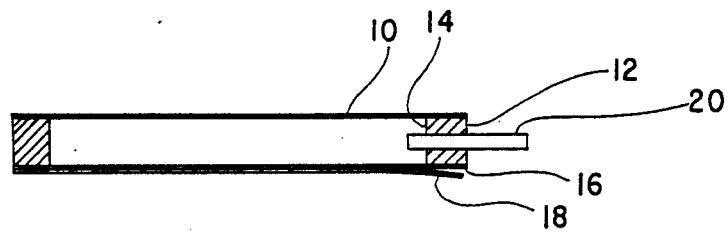
FIG. 2 is a cross sectional view thereof.
Figure 3:
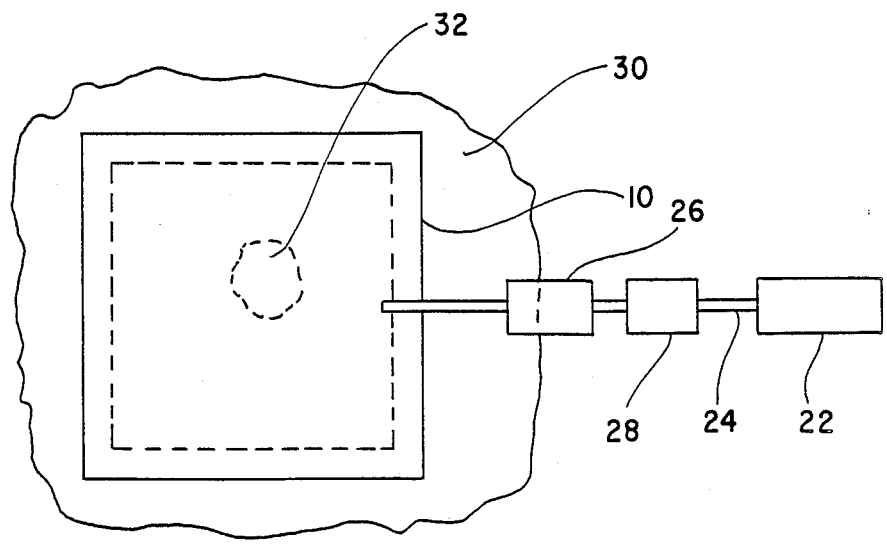
FIG. 3 s a perspective view of the preferred embodiment of the invention as connected to an oxygen feed system.

Referring now to FIG. 1-3, a thin flexible clear plastic film 10, which can be composed of polyurethane, has a typical thickness of 0.003-0.005 inches and defines a square of about 5 inches on a side. The film is impervious to the passage or leakage of oxygen therethrough.

A rigid hollow square shaped flat plastic member having an open cell structure 12, which can be composed of polyurethane foam, has a typical thickness of ⅛-½ inches, an outer perimeter 5 inches on a side and an inner perimeter 4 inches on a side, thus having a square shaped opening 14 of about 4 inches on a side. The open cell structure permits oxygen to leak therethrough.

The lower surface of the sheet is bonded, as for example by sonic welding or induction heating, to the upper surface of the member in an oxygen impervious manner. The lower surface of the member is coated with a self adhesive coating 16. This coating not only adheres to to the surface of the member but will also adhere to the skin of the patient when the dressing is put into use. Prior to use the adhesive coating is covered by release paper 18 which is easily removed to expose the coating immediately before use.

A hollow tube 20 can be composed of oxygen impervious polyurethane tubing and extends from the outside of the member into the central opening. This tube is also bonded to the member in an oxygen impervious manner to prevent oxygen from leaking back from the opening in the region of the member immediately surrounding the tube.

Oxygen from a suitable source such as a pressurized tank of oxygen 22 is supplied to the outer end of the tube via oxygen feed line 24. A pressure reducing valve 26, manually controllabe to adjust the pressure of oxygen fed to the tube is disposed in the line. A manually controlled on-off valve 28 is connected in the line between the tank and the pressure reducing valve In use, with valve 28 in the off position, the release paper is removed and the adhesive coated surface of the member is secured detachably to the skin 30 of the patient with the sore 32 disposed in the central opening in the member. The valve 28 is opened, and the valve 26 is adjusted until in the steady state the film exhibits a slight upward bulge in the region of the central opening. This bulge indicates that the oxygen pressure in the central region is slightly above the ambient air pressure outside of the dressing. The oxygen leakage through the open cell structure of the member is relatively slow so that the optimum pressure conditions can be maintained without difficulty during the period of the treatment.

What is claimed is:

1. Disposable hyperbaric oxygen dressing adapted to treat a body sore on the skin of a patient, said dressing comprising:

a thin flexible oxygen impermeable plastic sheet having upper and lower surfaces;

a rigid flat open cell plastic member which is oxygen permeable, the member having a central opening, a flat upper member surface and a flat lower member surface, the upper member surface being sealed to the lower surface of the sheet, sheet-member seal being oxygen impermeable, the lower member surface being adapted to be removably sealed to the skin of the patient with the sore being disposed in the central opening, the skin-member seal being oxygen impermeable;

an oxygen impermeable oxygen feed tube extending through the member into the central opening, the tube being sealed to the member, the tube-member seal being oxygen impermeable, the tube having opposite open ends, one end being positioned in the central opening, the other end being positioned outside of the member, the dressing being securable to the body with the lower member surface engaging the skin of a patient with the sore to be treated disposed in the centrol opening;

means disposed outside of the member and connected to said other end to supply oxygen under pressure to said opening to contact the sore, the oxygen within the opening leaking out of open cell structure of the member; and means to adjust the pressure of the supplied oxygen relative to the rate of oxygen leakage so that the pressure of oxygen in the central opening is positive with respect to ambient air pressure.

2. Disposable hyperbaric oxygen desssing adapted to treat a body sore on the skin of a patient as set forth in claim 1 and further including:

a first self-adhesive layer secured to the lower member surface and a second layer of release paper being removably secured to the first layer; the first layer, after the second layer has been removed, being adapted to be removably sealed to the skin of the patient with the sore being disposed in the central opening.

3. The dressing of claim 1 wherein the sheet is transparent.

4. The dressing of claim 3 wherein the member is composed of polyurethane foam, the sheet is composed of closed cell polyurethane film, and the tube is composed of polyurethane tubing.

* * * * *